(12) United States Patent
Harris et al.

(10) Patent No.: US 10,076,345 B2
(45) Date of Patent: *Sep. 18, 2018

(54) PATELLAR CLAMPING INSTRUMENT

(71) Applicant: MICROPORT HORTHOPEDICS HOLDINGS INC., Tiel (NL)

(72) Inventors: Brian R. Harris, Cordova, TN (US); Rick W. Wright, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/683,433

(22) Filed: Aug. 22, 2017

(65) Prior Publication Data

US 2017/0348012 A1 Dec. 7, 2017

Related U.S. Application Data

(60) Continuation of application No. 15/180,047, filed on Jun. 12, 2016, now Pat. No. 9,737,317, which is a division of application No. 13/918,429, filed on Jun. 14, 2013, now Pat. No. 9,364,245.

(60) Provisional application No. 61/660,250, filed on Jun. 15, 2012.

(51) Int. Cl.
*A61B 17/17* (2006.01)
*A61F 2/46* (2006.01)

(52) U.S. Cl.
CPC .......... *A61B 17/1767* (2013.01); *A61F 2/461* (2013.01); *A61F 2002/4622* (2013.01)

(58) Field of Classification Search
CPC ....... A61B 17/17; A61B 17/1767; A61F 2/46; A61F 2/461
See application file for complete search history.

(56) References Cited

U.S. PATENT DOCUMENTS 9,364,245 B2 * 6/2016 Harris ................ A61B 17/1767

* cited by examiner

*Primary Examiner* — Christopher Beccia
(74) *Attorney, Agent, or Firm* — Adams and Reese LLP

(57) ABSTRACT

A patellar clamp and associated system and method for using the clamp are provided. A patellar clamp includes a pair of handles movably coupled together, a patella support portion connected to the pair of handles and configured to engage a first side of a patella, and a reamer guide configured to engage a second side of the patella. The patella support portion and the reamer guide each include a first pair of flanges configured to engage a first and second tendon associated with the patella. The reamer guide is configured to allow reaming and resurfacing the entire desired posterior articular surface of the patella in a single operation without readjusting the position of the reamer guide.

15 Claims, 11 Drawing Sheets

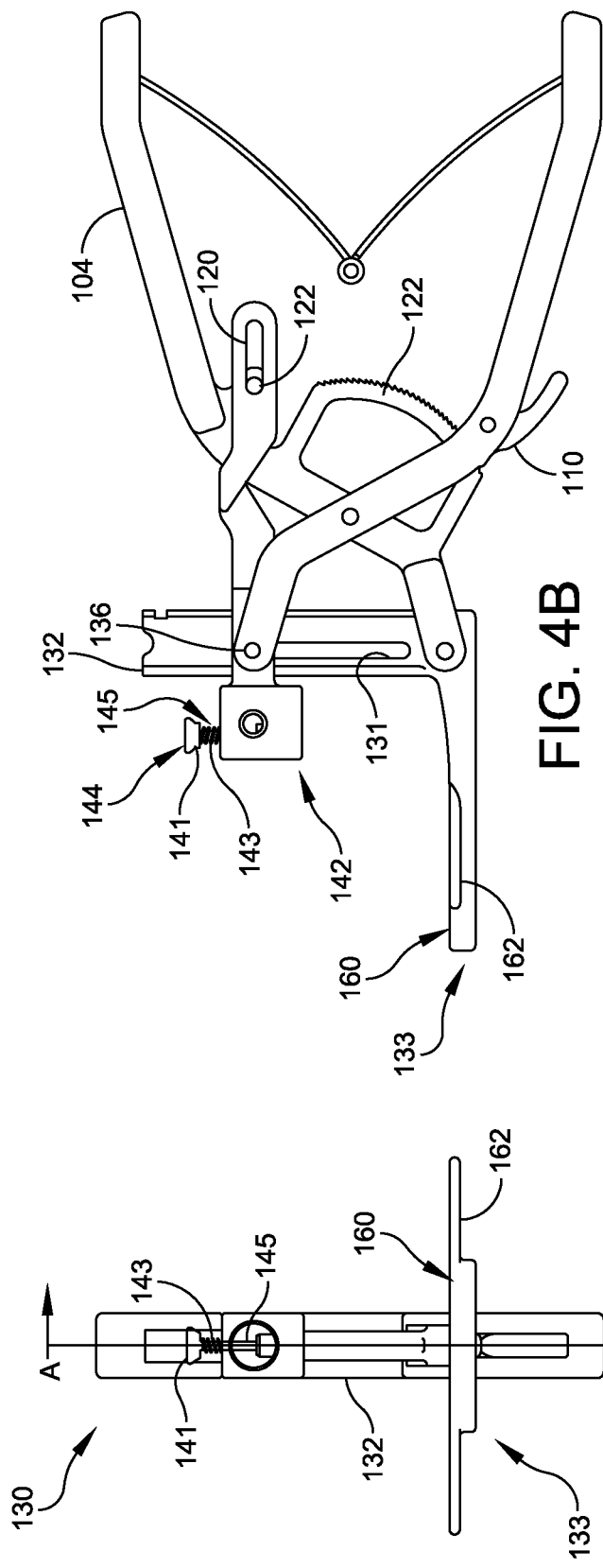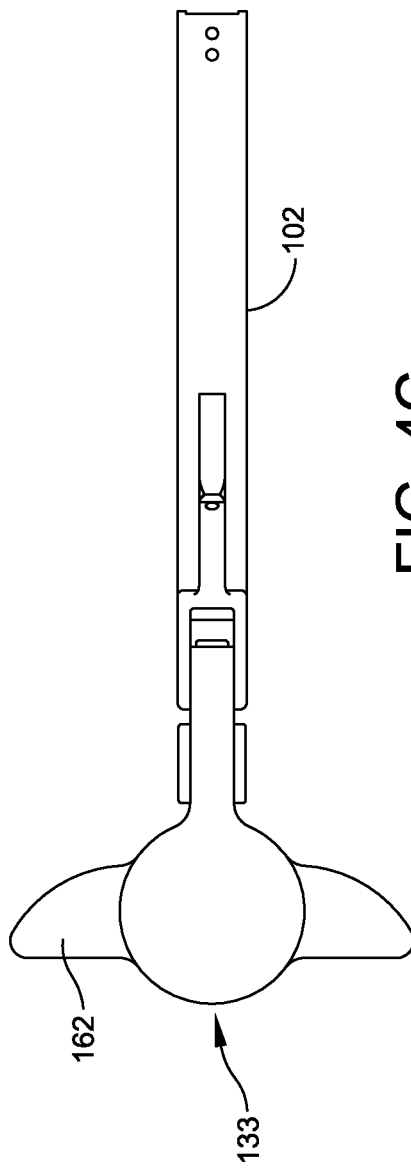

SECTION A-A

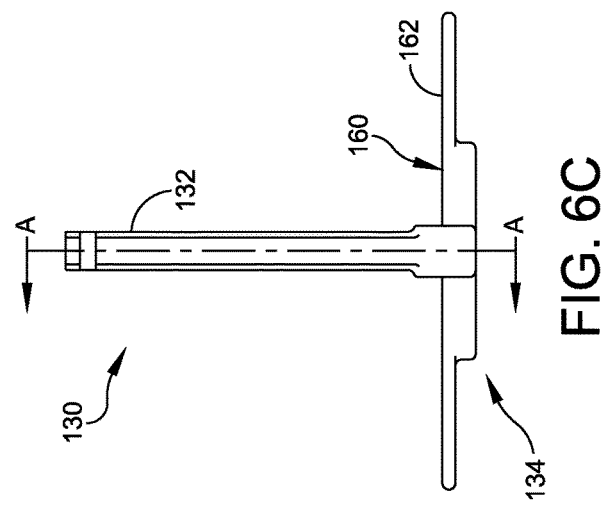
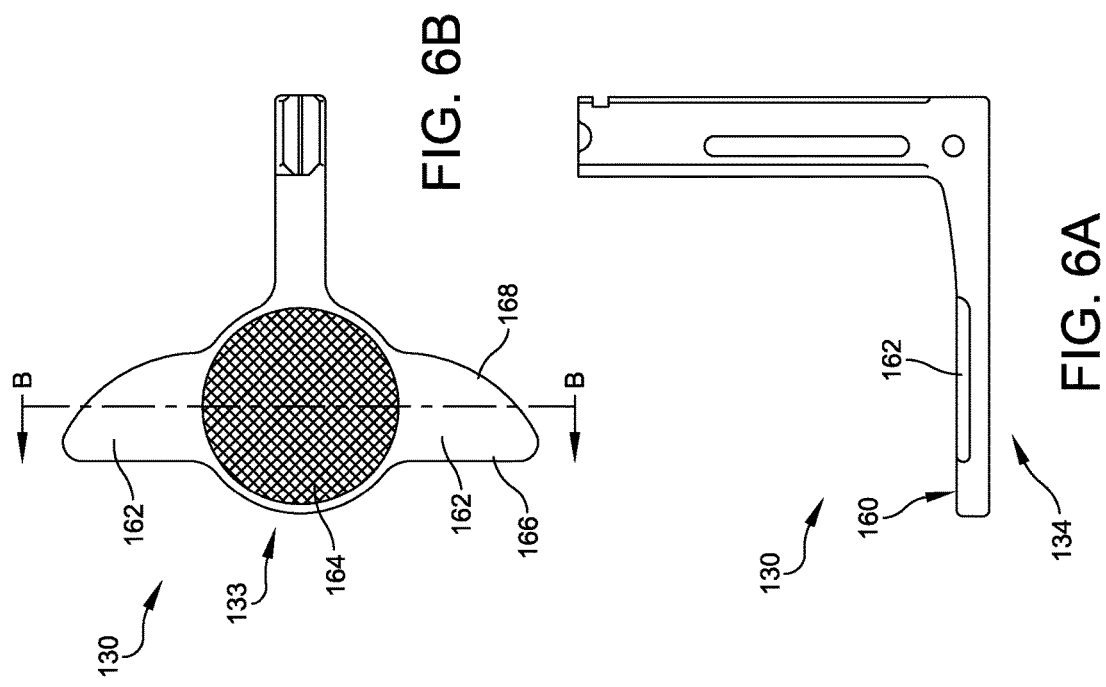

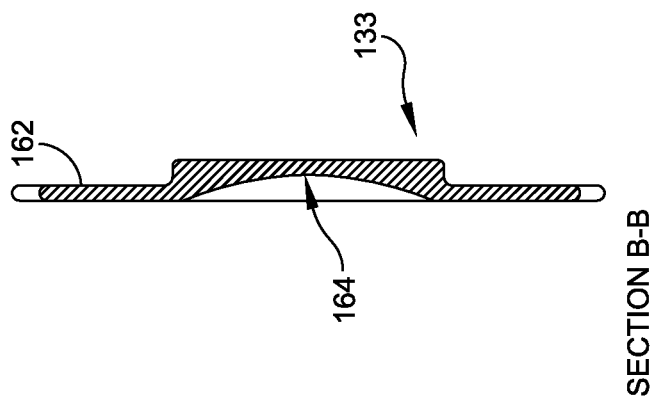
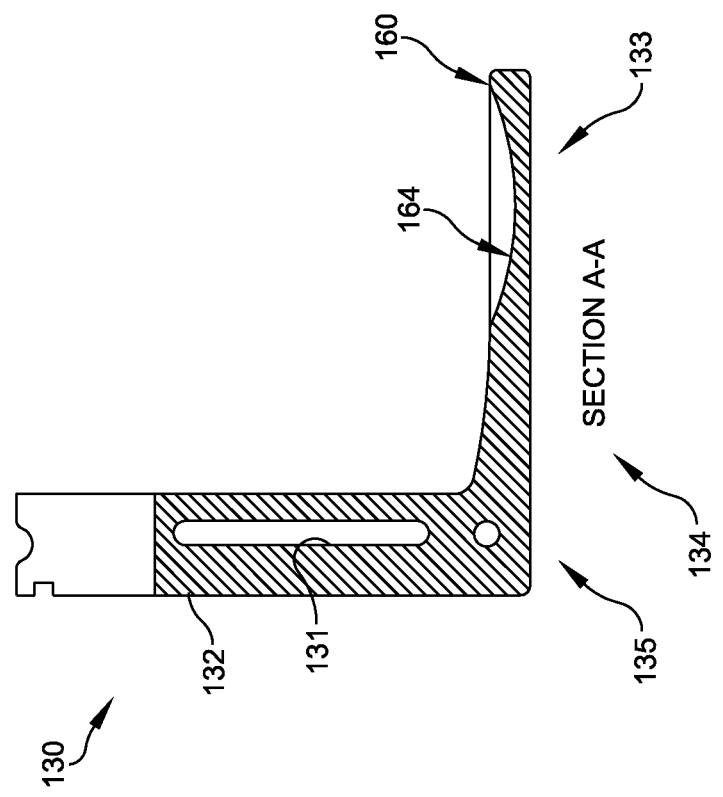

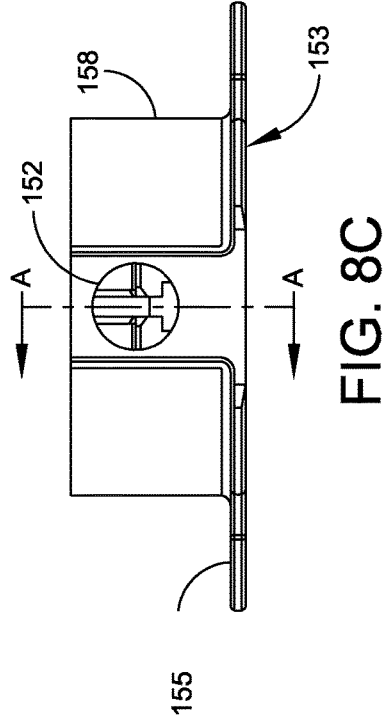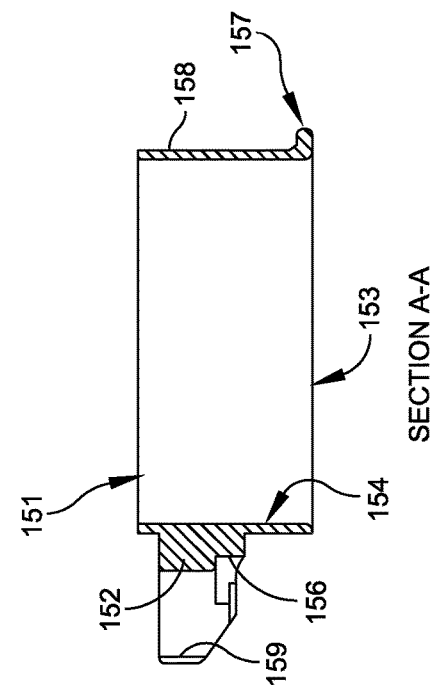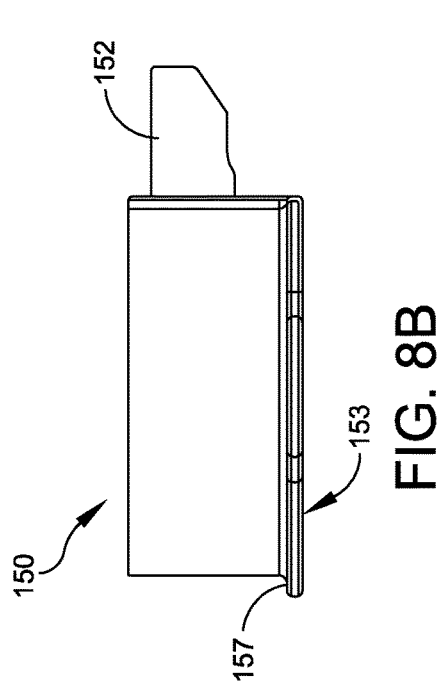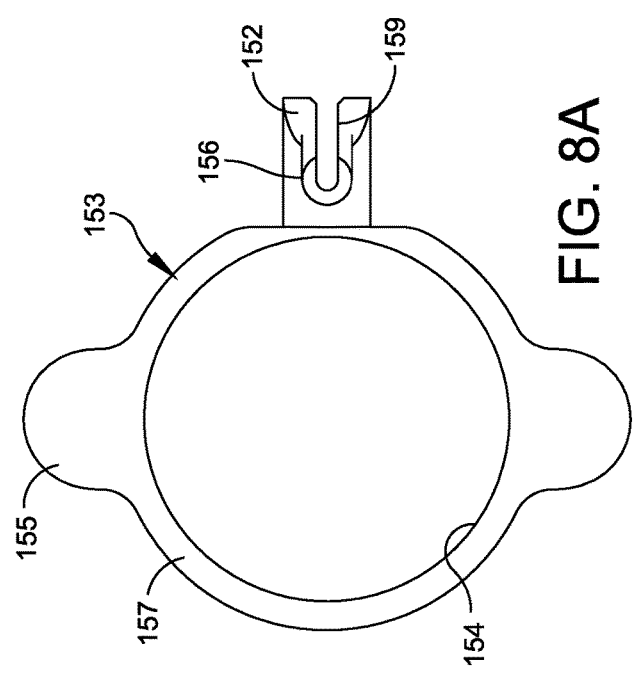

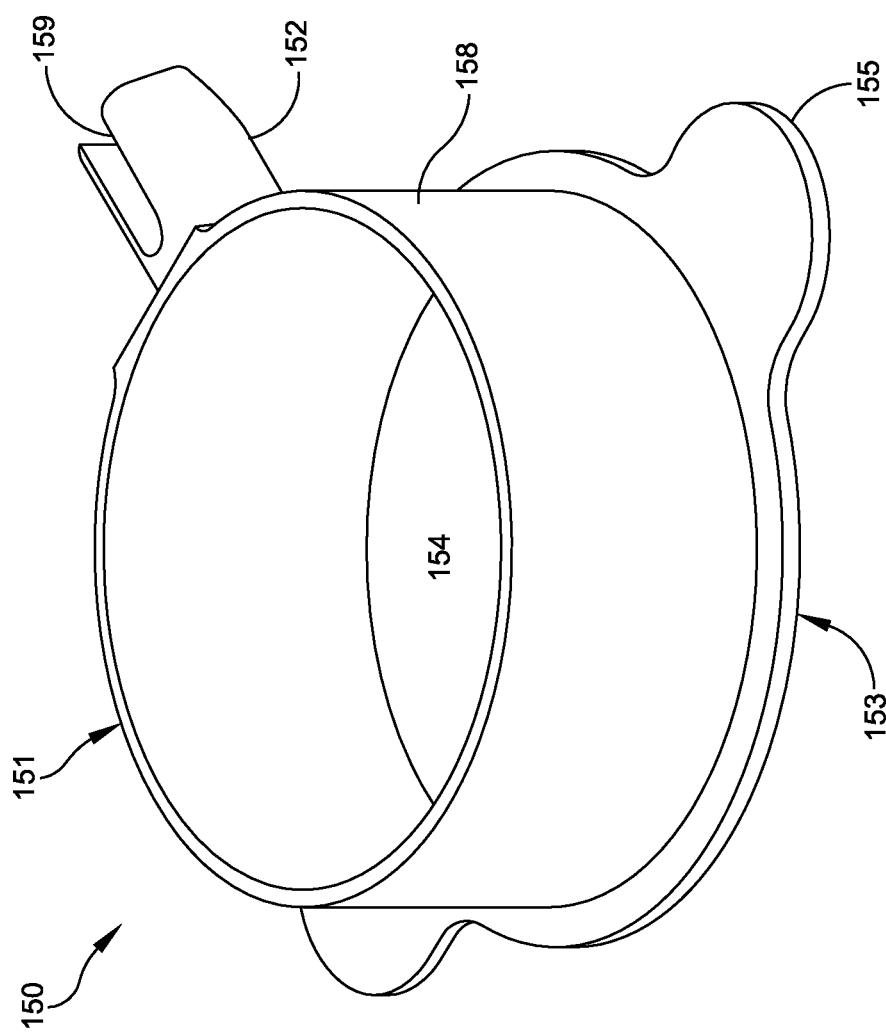

PATELLAR CLAMPING INSTRUMENT

PRIORITY CLAIM

This application claims priority U.S. patent application Ser. No. 15/180,047, filed Jun. 12, 2016, which issued as U.S. Pat. No. 9,737,317 on Aug. 22, 2017; U.S. patent application Ser. No. 13/918,429, filed Jun. 14, 2013, which issued as U.S. Pat. No. 9,364,245 on Jun. 14, 2016, the entirety of which is incorporated herein by reference, and to U.S. Provisional Patent Application No. 61/660,250, filed Jun. 15, 2012, the entirety of which is herein incorporated by reference.

BACKGROUND OF THE DISCLOSURE

The present disclosure generally relates to surgical instruments, and more particularly to an instrument and associated method for clamping the patella during a surgical procedure.

Surgical joint repair and replacement involving the knee includes resurfacing and preparing the posterior articular surface of the patella (knee cap) to accept a prosthetic patellar implant. FIG. 1 shows the typical anatomy of a knee. In some cases, resurfacing of this bone is accomplished by milling or planing the surface of the patella using a powered reamer having cutting teeth. During the surgical procedure, the patella is everted involving rotating and inverting the patella by approximately 45-180 degrees to gain access to the posterior surface for reaming and resurfacing.

A patellar clamp is used to hold the patella in the everted position for reaming. The anterior and posterior surfaces of the patella are clamped between a lower fixed platform and an upper adjustable reamer guide which can be varied in distance from the platform to accommodate the thickness of the patella. The reamer guide is generally tubular shaped and functions to rotatably confine the reamer therein during the milling/planing procedure. For stable support of the reamer guide and patella during reaming, the bottom annular edge of the guide generally includes sharp and pointed teeth for gripping the posterior articular surface of the patella to be resurfaced. The teeth also resist twisting of the patella during reaming.

The foregoing arrangement, however, restricts the amount of patellar surface area that is available for reaming which is not occupied by engagement with the bottom edge of the guide and teeth. Sufficient purchase should be available on the patella to engage the guide teeth for reaming stability, resulting in the use of a reamer guide smaller in diameter than ideal and thereby further restricting the surface area of the patella available for reaming. This may result in un-resurfaced bone around the periphery of the patella. Often, the surgeon must therefore reposition the reamer clamp and reamer to access the outer regions of the patella posterior articular surface. This causes the teeth on the reamer guide to sometimes engage portions of the quadriceps and patellar tendons when clamped to the patella, which causes trauma to the tendons.

SUMMARY OF THE DISCLOSURE

A patellar clamp and associated system and method for using the clamp are provided. In some embodiments, a patellar clamp comprises a pair of handles movably coupled together, a patella support portion operatively connected to the pair of handles and configured to engage a first side of a patella, and a reamer guide configured to engage a second side of the patella. The patella support portion and the reamer guide each include a first pair of flanges configured to engage a first and second tendon associated with the patella. The reamer guide is configured to allow reaming and resurfacing a predetermined portion of an articular surface of the patella in a single operation without readjusting the position of the reamer guide.

In some embodiments, a method of clamping a patella is provided. The method includes selecting, from a plurality of reamer guides, a reamer guide configured to enable reaming a predetermined portion of a patellar surface. The selected reamer guide is configured with a first pair of flanges extending from the reamer guide. The method also includes attaching the selected reamer guide to a patellar clamp including a pair of handles and a bottom clamping arm with a patellar support portion and a second pair of flanges. The method includes placing the patellar clamp in an open position, positioning an everted and rotated patella between the selected and attached reamer guide and the patellar support portion of the bottom clamping arm, and squeezing the pair of handles together in a closing motion, causing the selected and attached reamer guide to lower toward the patella and the first pair of flanges and the second pair of flanges to operably engage the quadriceps tendon and patellar tendon.

In some embodiments, a system for clamping a patella is provided. The system includes a patellar clamp comprising a pair of handles movably coupled together, a patella support portion operatively connected to the pair of handles via a bottom clamping arm and configured to engage a first side of a patella, the patella support portion including a first pair of flanges each configured to engage a first and second tendon associated with the patella and a plurality of reamer guides, each reamer guide of said plurality having a different diameter than each other reamer guide of said plurality to allow a user to select an appropriately-sized reamer guide, wherein each reamer guide is configured to engage a second side of the patella, each reamer guide including a second pair of flanges configured to engage said first and second tendons associated with the patella.

BRIEF DESCRIPTION OF THE DRAWINGS

FIGS. 4A, 4B, and 4C are front, side, and bottom profile views of a patellar clamp in accordance with some embodiments of the present disclosure.

FIGS. 6A, 6B, and 6C are side, top, and rear profile views, respectively, of a bottom clamping arm of the patellar clamp in accordance with some embodiments of the present disclosure.

FIGS. 7A and 7B are cross-sectional side and front views, respectively, of a bottom clamping arm of the patellar clamp in accordance with some embodiments of the present disclosure taken along lines A-A and B-B in FIG. 6.

FIGS. 8A, 8B, 8C, and 8D are bottom, side, rear, and cross-sectional side profile views, respectively, of a reamer guide of the patellar clamp in accordance with some embodiments of the present disclosure.

FIG. 9 is an isometric view of the top of a reamer guide of the patellar clamp in accordance with some embodiments of the present disclosure.

DETAILED DESCRIPTION

Figure 1:
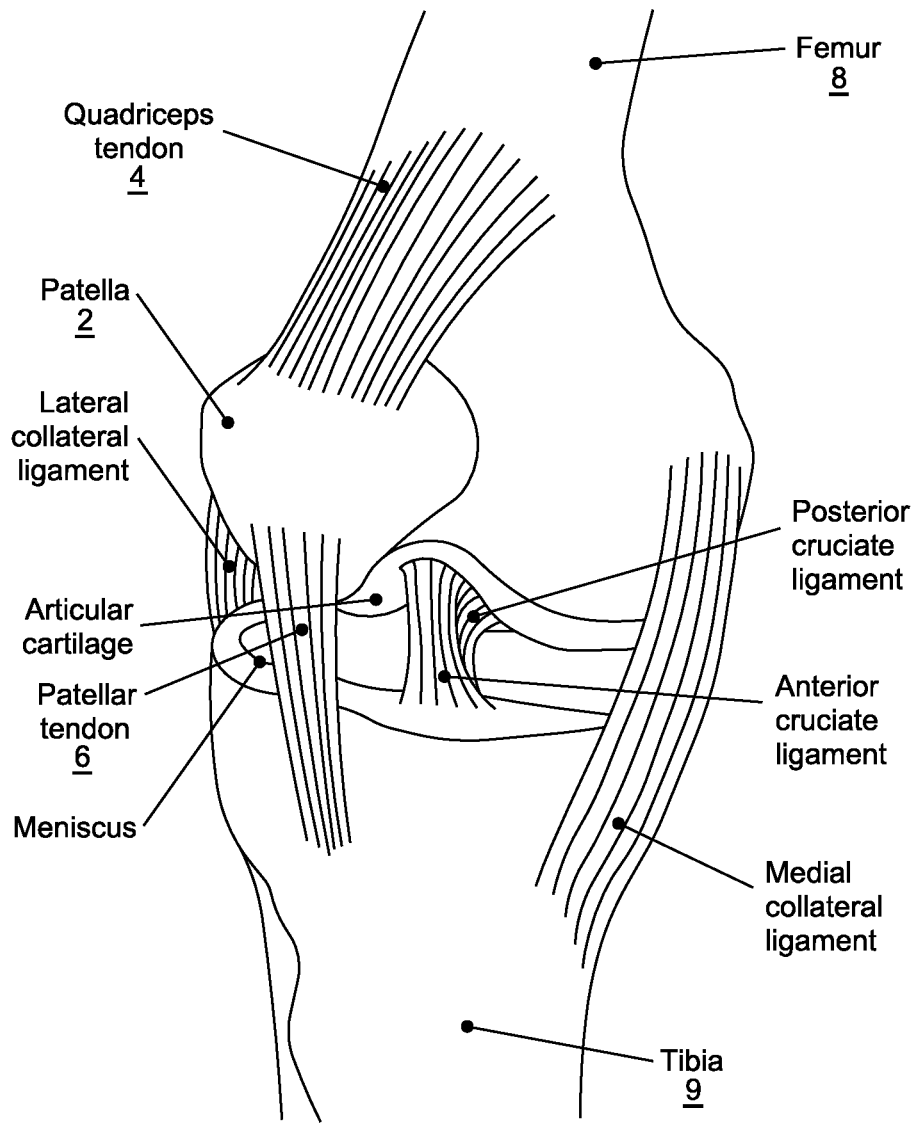
FIG. 1 is a cutaway view of the typical anatomy of the knee.

With reference to the Figures, where like elements have been given like numerical designations to facilitate an understanding of the drawings, the various embodiments of a patellar clamp and associated system and method for using the clamp are described. The figures are not drawn to scale.

The following description is provided as an enabling teaching of a representative set of examples. Those skilled in the art will recognize that many changes can be made to the embodiments described herein while still obtaining beneficial results. It will also be apparent that some of the desired benefits discussed below can be obtained by selecting some of the features or steps discussed herein without utilizing other features or steps. Accordingly, those who work in the art will recognize that many modifications and adaptations, as well as subsets of the features and steps described herein are possible and can even be desirable in certain circumstances. Thus, the following description is provided as illustrative and is not limiting.

This description of illustrative embodiments is intended to be read in connection with the accompanying drawings, which are to be considered part of the entire written description. In the description of embodiments disclosed herein, any reference to direction or orientation is merely intended for convenience of description and is not intended in any way to limit the scope of the present invention. Relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation. Terms such as "attached," "affixed," "coupled", "connected," and "interconnected," refer to a relationship wherein structures are secured or attached to one another either directly or indirectly through intervening structures, as well as both movable or rigid attachments or relationships, unless expressly described otherwise. Accordingly, the disclosure expressly should not be limited to such embodiments illustrating some possible non-limiting combination of features that may exist alone or in other combinations of features.

FIG. 1 is a cutaway view of the typical anatomy of the knee, provided for a general understanding of the region in which the present disclosure is to be used. Of interest to the present disclosure, a patella 2 is held in place over the knee joint by a quadriceps tendon 4 and a patellar tendon 6. Quadriceps tendon 4 links the patella 2 with the femur 8, while patellar tendon 6 links the patella 2 with the tibia 9.

Figure 2:
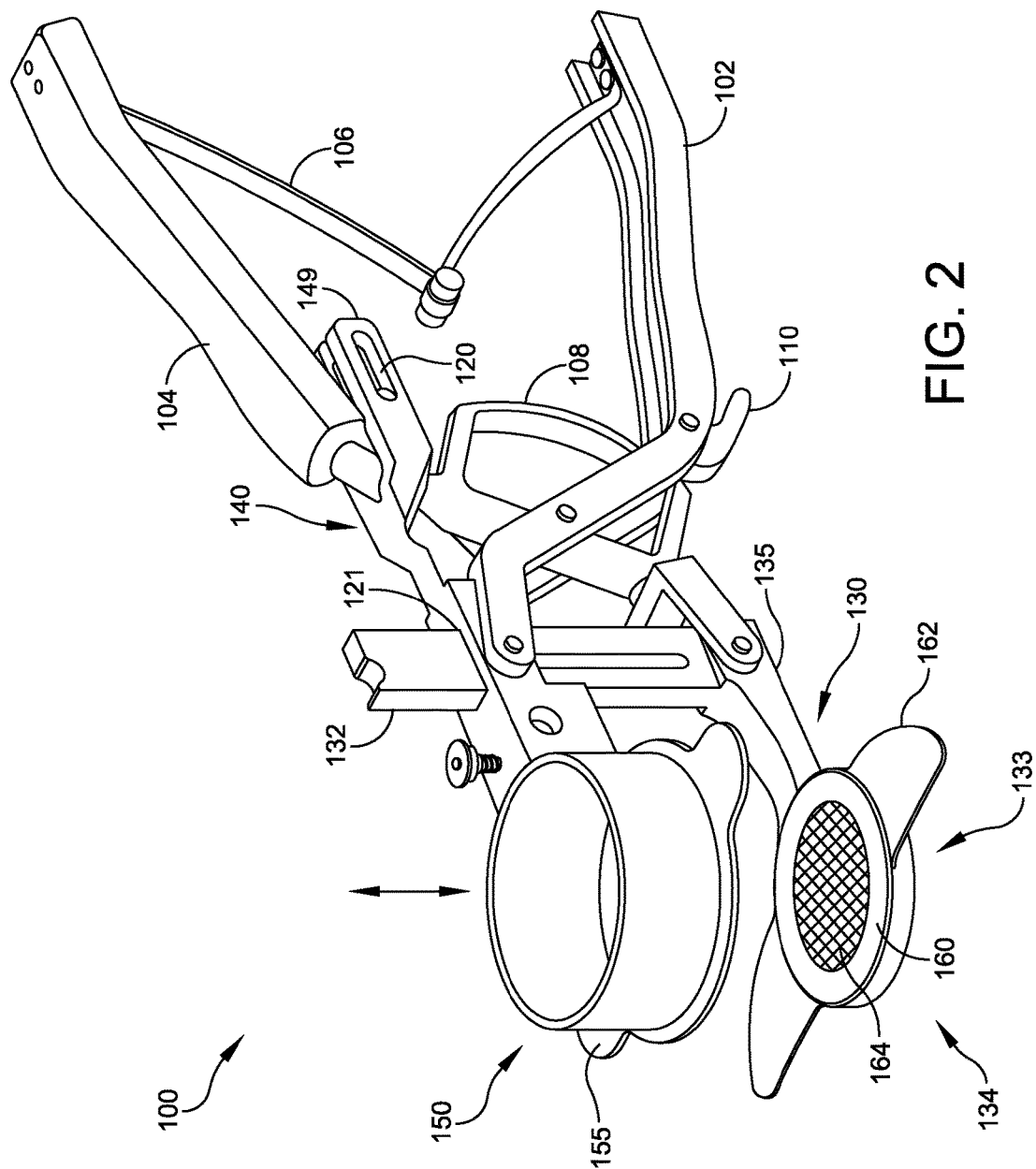
FIG. 2 is an isometric view of a patellar clamp in accordance with some embodiments of the present disclosure.
Figure 3:
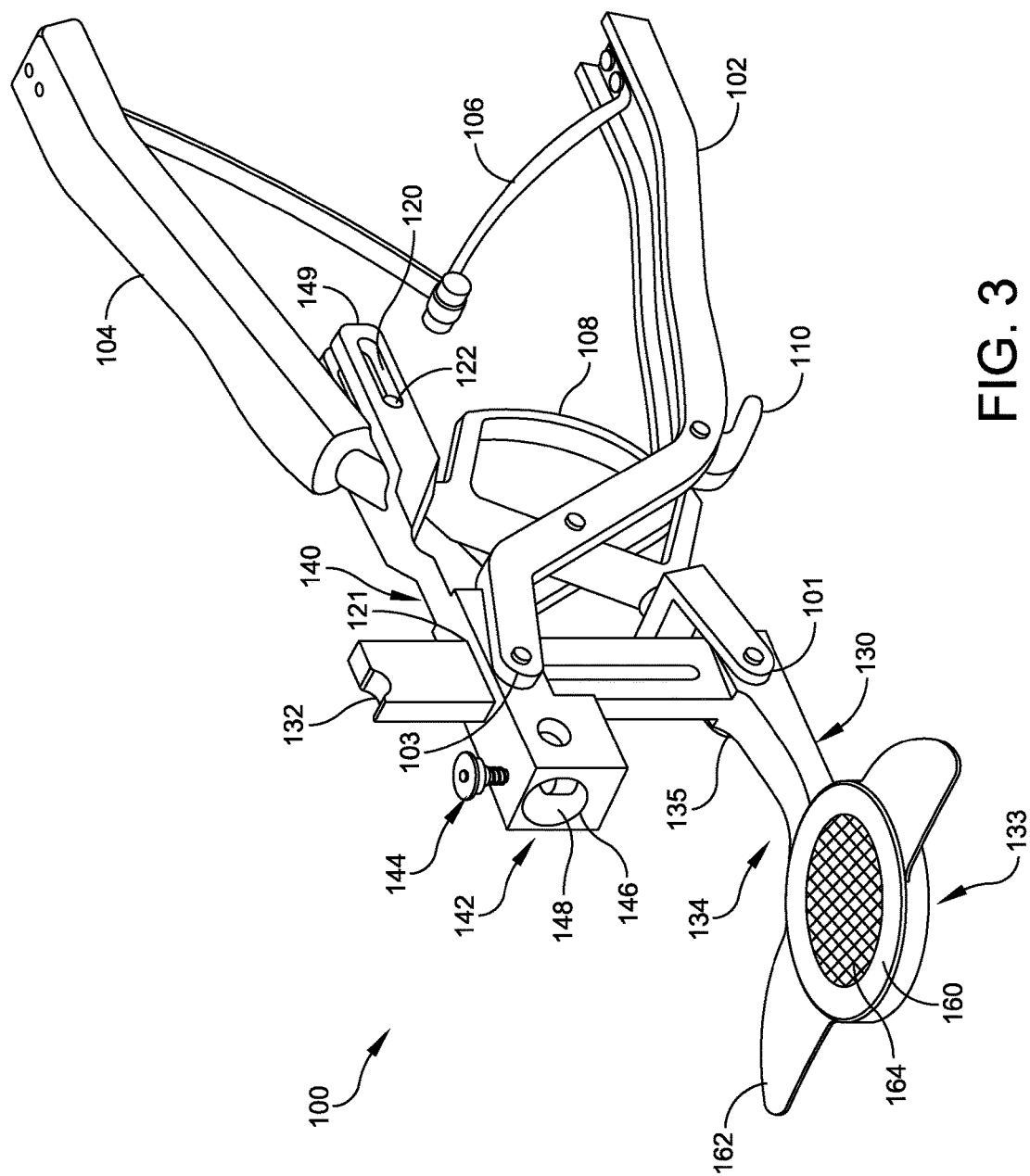
FIG. 3 is an isometric view of a patellar clamp with the reamer guide removed in accordance with some embodiments of the present disclosure.
Figure 5:
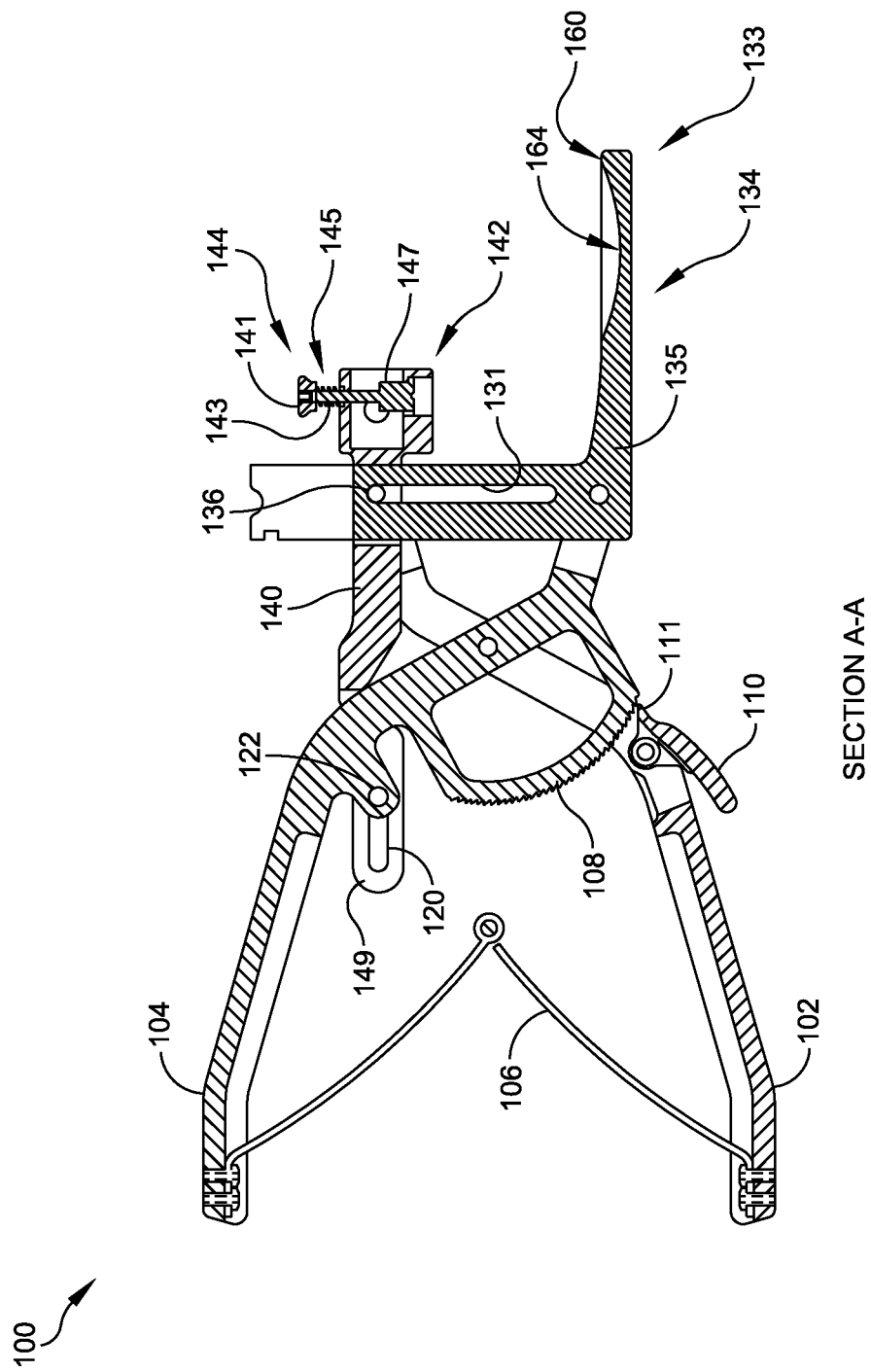
FIG. 5 is a cross-sectional side view of the patellar clamp in accordance with some embodiments of the present disclosure taken along line A-A of FIG. 4.

FIGS. 2-5 provide views of an exemplary embodiment of the present disclosure. FIG. 2 is an isometric view of a patellar clamp 100 of an exemplary embodiment of the present disclosure. FIG. 3 is an isometric view of a patellar clamp 100 with reamer guide 150 removed in an exemplary embodiment of the present disclosure. FIGS. 4A, 4B, and 4C are front, side, and bottom profile views of a patellar clamp 100 of an exemplary embodiment of the present disclosure. FIG. 5 is a cross-sectional side view of the patellar clamp 100 of an exemplary embodiment of the present disclosure taken along line A-A of FIG. 4.

Referring now to FIGS. 2-5, patellar clamp 100 includes a lower handle 102 and upper handle 104, pivotally coupled together with a compression leaf spring 106 biasing the handles apart. The distal end 101 of upper handle 104 is pivotally coupled to bottom clamping arm 130. Upper handle 104 further includes a toothed ratchet bar 108 which is engageable with a pawl 111 disposed on a locking lever 110 pivotally mounted on lower handle 102 for locking the handle into position when the desired clamping pressure on the patella 2 is achieved.

The distal end 103 of lower handle 102 is pivotally coupled to a sliding top clamp arm 140 which is slidable up and down on a reamer support column 132 of bottom clamping arm 130 configured to mount the outrigger of a reamer assembly (not shown) thereto. Suitable reamers and reamer assemblies useable with patellar clamp 100 include the Advance® Patellar Reaming System commercially available from Wright Medical Technology, Inc. of Arlington, Tenn. Embodiments of top clamp arm 140 include an opening 121 for receiving reamer support column 132 completely therethrough as shown in FIGS. 2 and 3.

Top clamp arm 140 includes a reamer guide mounting bracket 142 configured to detachably receive and mount thereto a reamer guide 150 shown in FIG. 2. With additional reference to FIGS. 3-5, mounting bracket 142 includes a frontal opening 146 communicating with an internal cavity 148 configured to insert a portion of a reamer guide mounting stem 152 therein to secure the reamer guide 150 (see also FIGS. 8-10). A spring-loaded plunger assembly 144 comprised of an elongated plunger 145 having an operating button 141 and spring 143 as further described herein is included with the mounting bracket assembly (see also FIGS. 4 and 5). Plunger 145 is cylindrically shaped in some embodiments including a stem extending through a top opening in the mounting bracket 142 into cavity 148 and including a diametrically enlarged portion 147 configured to engage a complementary sized and configured socket 156 disposed in the stem 152 of reamer guide 150. The plunger assembly allows the reamer guide to be detachably mounted to the patellar clamp 100, as further described herein.

Top clamp arm 140 further includes a U-shaped rear bifurcated portion comprised of a pair of spaced-apart legs 149 which extend around a portion of upper handle 104 received therebetween as shown in FIGS. 2-5. The legs 149 can include elongated slots 120 configured to slidably receive a dowel pin 122 having one end affixed to upper handle 104 for guiding movement and supporting sliding top clamp arm 140.

FIGS. 6 and 7 are directed to bottom clamping arm 130. FIGS. 6A, 6B, and 6C are side, top, and rear profile views, respectively, of a bottom clamping arm 130 of the patellar clamp 100 in accordance with some embodiments of the present disclosure. FIGS. 7A and 7B are cross-sectional side and front views, respectively, of a bottom clamping arm 130 of the patellar clamp 100 in accordance with some embodiments of the present disclosure taken along lines A-A and B-B in FIG. 6.

Referring now to FIGS. 2-7, bottom clamping arm 130 includes a patella support base 134 and reamer support column 132. In some embodiments, patella support base 134 and reamer support column 132 are formed as integral unitary structural components of bottom clamping arm 130. Reamer support column 132 is disposed perpendicular to patella support base 134 and is vertically elongated. Reamer support column 132 includes an elongated slot 131 which receives a dowel pin 136 therethrough (see FIG. 5) for sliding upward and downward movement. Dowel pin 136 movably couples lower arm 102 and top clamp arm 140 together at the column. In operation, opening and closing the lower handle 102 and upper handle 104 correspondingly moves top clamp arm 140 up and down with respect to reamer support column 132 and patella support base 134 to provide patella clamping action.

With continuing reference to FIGS. 2-7, patella support base 134 of bottom clamping arm 130 is horizontally elongated and includes a proximal portion 135 adjoining reamer support column 132 and a diametrically enlarged distal patella support portion 133 (hereafter distal portion 133) configured to engage the patellar bone. In some embodiments, distal portion 133 is disposed perpendicular or 90 degrees to reamer support column 132.

In some embodiments, distal portion 133 is substantially circular in configuration when viewed from the top (see FIG. 6B). Distal portion 133 of bottom clamping arm 130 includes a substantially planar top surface 160 including a concave shaped gripping region 164 centrally located on the top surface 160. The gripping region 164 can be contoured to match the prominence or convex shape of the anterior side of the patella 2 to improve clamping and immobilizing the patella 2 during reaming. In some embodiments, gripping region 164 includes a textured surface treatment configured to increase frictional grip between the gripping region 164 and patella 2. In some embodiments, the textured surface can include diamond-shaped teeth to positively grip the anterior surface of the patella 2 and resist twisting of the patella 2 during reaming of the opposite posterior surface of the patella 2. In one representative embodiment, the textured surface can be 0.060- to 0.080-inch cross pattern diamond-shaped teeth. Other suitable textured surface configurations and gripping features are contemplated and can be used. The concave gripping region 164 can cover substantially the majority, and in some embodiments substantially the entire top surface 160 of the enlarged circular distal portion 133 of the bottom clamping arm 130. As opposed to long spikes used heretofore in some embodiments, the diamond patterned gripping surface improves grip and stability of the patella 2 during reaming and is less intrusive on the patellar bone.

With continuing reference to FIGS. 2-7, enlarged distal portion 133 of bottom clamping arm 130 includes a pair of diametrically opposed and elongated flanges 162 configured to grasp the quadriceps tendon 4 and patellar tendon 6 on opposing sides of the patella 2 (see, e.g., FIG. 1). In some embodiments, flanges 162 are arranged 180 degrees apart to complement the same arrangement of the quadriceps tendon 4 and patellar tendon 6 with respect to the patella 2 (see FIG. 1). In some embodiments flanges 162 extend radially outwards from distal portion 133 in a direction perpendicular to lower handle 102 and upper handle 104. In some embodiments, as best shown in FIG. 6, flanges 162 can include a substantially flat side distal edge 166 and an opposing arcuate proximal side 168 closest to lower handle 102 and upper handle 104 to conform to the shape of the tendons when twisting during eversion and rotation of the patella 2 upon clamping to minimize trauma to the tendons.

Figure 10:
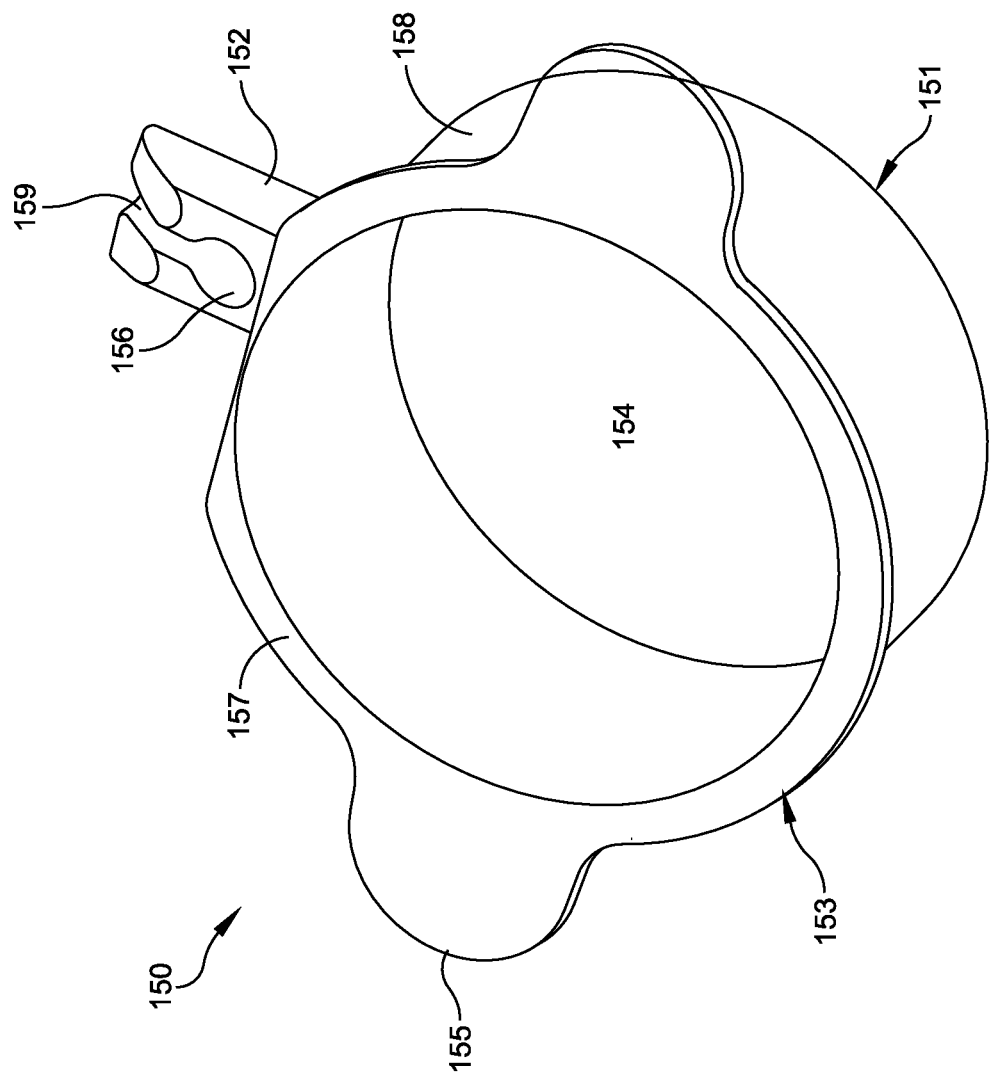
FIG. 10 is an isometric view of the bottom of a reamer guide of the patellar clamp in accordance with some embodiments of the present disclosure.

FIGS. 8-10 are directed to reaming guide 150. FIGS. 8A, 8B, 8C, and 8D are bottom, rear, side, and cross-sectional side profile views, respectively of a reamer guide 150 of the patellar clamp 100 in accordance with some embodiments of the present disclosure. FIG. 9 is an isometric view of the top of a reamer guide 150 of the patellar clamp 100 in accordance with some embodiments of the present disclosure. FIG. 10 is an isometric view of the bottom of a reamer guide 150 of the patellar clamp 100 in accordance with some embodiments of the present disclosure. FIG. 2 additionally shows reaming guide 150 connected to the patellar clamp 100.

Reaming guide 150 is generally tubular and hollow shaped defining an annular sidewall 158 extending between annular top edge 151 and annular bottom edge 153. In some embodiments, bottom edge 153 engages the quadriceps tendon 4 and patellar tendon 6 and is a relatively smooth, plain surface without textures or teeth. Sidewall 158 defines a central passageway 154 that extends completely through the reaming guide 150 (see FIGS. 8-10), and which is sized and configured to rotatably receive a reamer (not shown) therein for milling and/or planing the posterior surface of the patella 2.

Reaming guide 150 further includes a pair of diametrically opposed and elongated flanges 155 configured to grasp the quadriceps tendon 4 and patellar tendon 6 on opposing sides of the patella 2 (see, e.g., FIG. 1). When the reaming guide 150 is mounted to patellar clamp 100, as shown in FIG. 2, flanges 155 extend radially outwards from sidewall 158 in a direction perpendicular to the lower handle 102 and upper handle 104. In some embodiments, flanges 155 are arranged 180 degrees apart to complement the same arrangement of the quadriceps tendon 4 and patellar tendon 6 with respect to the patella 2 (see FIG. 1). In some embodiments, flanges 155 are disposed adjacent to bottom edge 153 thereby being positioned to engage the tendons. Flanges 155 are positioned for vertical alignment with flanges 162 of bottom clamping arm 130 to provide clamping action when combined for grasping and holding the quadriceps tendon 4 and patellar tendon 6 during the reaming operation. Flanges 155 and 162 will be disposed on the top and bottom sides of the tendons, respectively, when clamped by patellar clamp 100. In various embodiments, flanges 155 and 162 can have substantially equal or different total radial widths measured from end-to-end of each flange. In some embodiments, flanges 162 can have a greater radial width than flanges 155.

To eliminate a narrow bottom edge for portions of sidewall 158 of the reamer guide 150 that can engage part of the quadriceps tendon 4 and patellar tendon 6, some embodiments of reamer guide 150 include a radially broadened bottom rim 157 disposed along bottom edge 153 (see FIGS. 8-10), thereby providing a generally flat bottom annular surface on guide 150 if the tendons might be engaged during clamping of patella clamp 100 onto the patella 2.

Referring primarily to FIGS. 8-10, reaming guide 150 includes a mounting stem 152 protruding radially outwards from a rear portion of sidewalls 158. Stem 152 includes a rearwardly open slot 159 and socket 156 configured to engage diametrically enlarged portion 147 of plunger 145. In some embodiments, socket 156 is downwardly open and communicates with slot 159 that receives the stem of plunger 145 therein. To mount the reamer guide 150 to mounting bracket 142 on top clamp arm 140, the spring-loaded plunger is first depressed to lower enlarged portion 147. The mounting stem 152 of reamer guide 150 is next inserted rearwardly into frontal opening 146 of the bracket, and the plunger is then released which seats the enlarged portion 147 in socket 156, thereby locking reamer guide 150 into the mounting bracket 142.

In some embodiments, reamer guide 150 has a diameter large enough to expose a maximum surface area of the posterior articular surface of the patella to be resurfaced. A reamer guide 150 of sufficient diameter avoids the need to unclamp, reposition, re-clamp, and ream peripheral portions of the posterior surface which were occluded by the reamer guide during an initial reaming operation. Advantageously, this is made possible by the configuration and size selected for the reamer guide 150 and smooth bottom edge 153 thereon giving the patellar clamp 100 the ability to clamp the quadriceps tendon 4 and patellar tendon 6 primarily with flanges 155 and 162 to support and stabilize the patella against torsion during reaming in lieu of gripping the posterior surface of the patellar bone to be resurfaced with teeth or other similar-shaped gripping features on the bottom edge of the reamer guide 150. In some embodiments, a diameter for reamer guide 150 can be selected that is slightly larger than the outer periphery of the posterior surface area of the patella 2 to be reamed and resurfaced for receiving a prosthetic implant. The reamer guide 150 can have a diameter that is at least larger than the area of the patella 2 lying between the quadriceps tendon 4 and patellar tendon 6 (see FIG. 1) to be resurfaced. In some embodiments, a patellar clamp 100 kit has reamer guides 150 of different diameters so a surgeon can select the appropriately sized reamer guide 150 to match the size of the patient's patella 2 and achieve the above-mentioned advantages when clamping the quadriceps tendon 4 and patellar tendon 6 using the reamer guide 150.

An exemplary method for clamping a patella 2 using patellar clamp 100 will now be briefly described. If a patellar clamp 100 kit is provided with a plurality of different diameter reamer guides 150, the surgeon first selects the appropriately sized reamer guide 150 to allow a single clamping and reaming step to be used for resurfacing a predetermined portion of the posterior articular surface of the patella 2. In some embodiments, the predetermined portion of the posterior articular surface of the patella 2 is the entire posterior articular surface of the patella 2 desired. This reamer guide 150 can have a diameter at least the same as or slightly larger than the outer periphery or diameter of the bone region to be resurfaced. The surgeon mounts the selected reamer guide 150 to patellar clamp 100 in the manner already described using the spring loaded plunger 145 resulting in a configuration of patellar clamp 100 shown in FIG. 2.

Patellar clamp 100 is adjusted as needed to an open position as shown in FIG. 2 with distal portion 133 of bottom clamping arm 130 spaced apart from reamer guide 150 by a distance sufficient to insert the patella 2 therebetween. The everted and rotated patella 2 is next positioned between bottom clamping arm 130 and reamer guide 150. The quadriceps tendon 4 and patellar tendon 6 will become twisted to a certain degree by the eversion depending on the degree of inverting the patella 2 that is used by the surgeon. The convex surface of the anterior surface of the patella 2 is positioned in alignment with and can be partially or fully engaged with concave-shaped gripping region 164 of bottom clamping arm 130. In some embodiments, concave-shaped gripping region 164 can include a textured gripping surface treatment such as diamond-shaped teeth to enhance the frictional grip on the patellar bone. At the same time, the quadriceps tendon 4 and patellar tendon 6 (see FIG. 1) are inserted and positioned between the mating pairs of flanges 155 and 162.

Lower handle 102 and upper handle 104 are next squeezed together in a closing direction by the user which is translated into a corresponding closing and clamping action of the bottom clamping arm 130 and reamer guide 150 attached to top clamp arm 140. Reamer guide 150 is lowered into engagement with substantially only the quadriceps tendon 4 and patellar tendon 6, with the smooth bottom edge 153 and flanges 155 of the guide engaging the tendons instead of the patella 2 bone. This is achieved by selecting a reamer guide 150 with a diameter larger than the posterior exposed patella 2 bone areas between the points on the bone where the tendons are attached (see FIG. 1). The clamping action grabs and holds the tendons firmly between the mating pairs of flanges 155 and 162 on the reamer guide 150 and bottom clamping arm 130. In some instances, since the geometry of the patella 2 is not perfectly circular but slightly irregular with somewhat triangular-circular combination of shapes (see FIG. 1), engagement of the reamer guide 150 with a minor peripheral portion of bone on posterior surface of the patella 2 not lying between the quadriceps tendon 4 and patellar tendon 6 (e.g. peripheral medial and/or lateral edges) can occur. However, the primary clamping forces for holding and immobilizing the patella 2 during reaming of the bone are between the reamer guide 150 and tendons in preferred embodiments.

Figure 11:
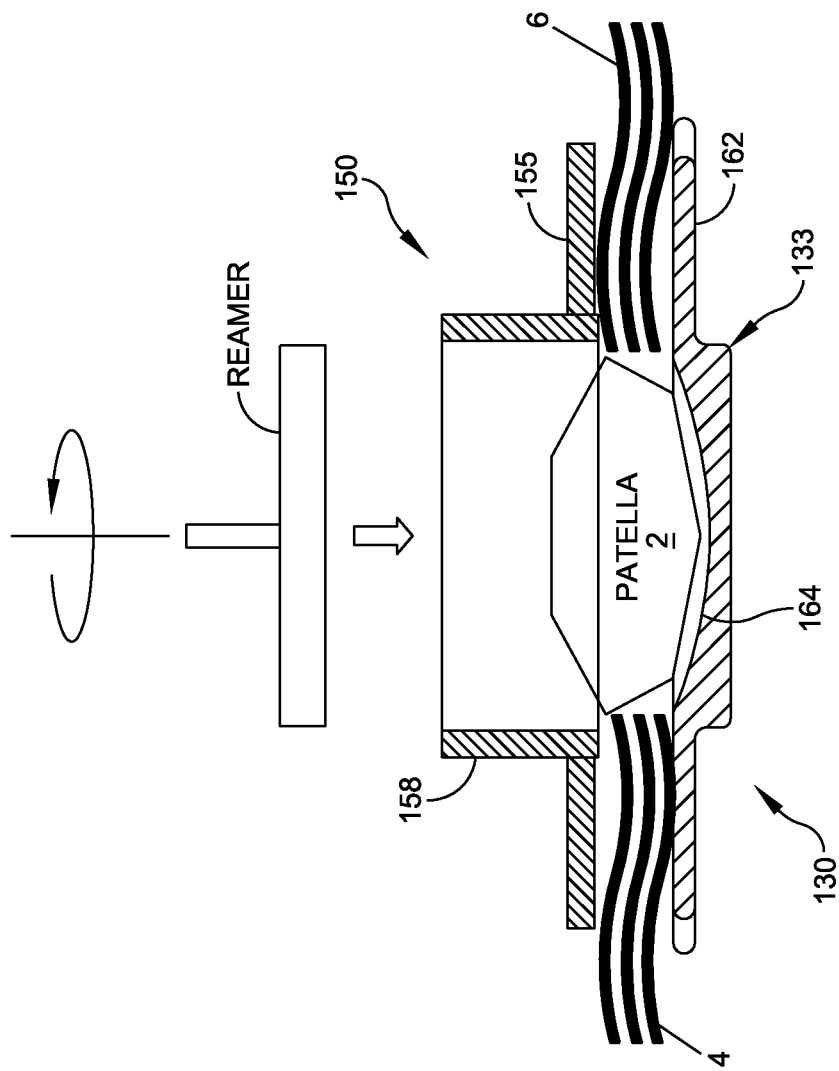
FIG. 11 is a cross-sectional front view of a patellar clamp, specifically the reamer guide and bottom clamping arm, engaged about the patella during reaming in accordance with some embodiments of the present disclosure.

A fully clamped patella 2 and tendons engaged by flanges 155 and 162 are shown in the cross-sectional front view of FIG. 11. Once the patella 2 is clamped, the position of lower handle 102, upper handle 104, and patellar clamp 100 can be locked by engaging locking lever 110 with ratchet bar 108. The reamer assembly (not shown) can then be mounted on patellar clamp 100 (if not already done before) and the reamer (see FIG. 11) positioned within reamer guide 150 to engage the patellar bone for resurfacing.

Once reaming is complete, the patellar clamp 100 can be removed by reversing the foregoing steps.

The components of patellar clamp 100 disclosed herein can be made of any suitable surgically-approved materials amenable to sterilization including metals, non-metals, and combinations thereof. In some embodiments, reamer guide 150 and bottom clamping arm 130 are made of ASTM A564-Type 630 martensitic precipitation hardened stainless steel. Other suitable materials can be used.

Advantages of the present embodiments of patellar clamp 100 according to the present disclosure include the ability to ream and resurface the entire desired posterior articular surface of the patella 2 in a single operation without readjusting the position of the reamer guide 150 for performing additional reaming steps around the peripheral surfaces of the patella 2. This is achieved in part by the mating flanges 155 and 162 which grasp and clamp the quadriceps tendon 4 and patellar tendon 6 to stabilize the reamer guide 150 during reaming allowing a larger diameter reamer guide 150 and reamer cutting head to be used. An additional advantage of some embodiments of patellar clamp 100 is that the soft tissue of the tendons is protected from trauma by eliminating the need for grasping teeth on the reamer guide 150 and thereby allowing for the provision of smooth surfaces on reamer guide 150 disclosed herein that engage the patella 2 and/or portions of the tendons.

In some embodiments, a clamping instrument is provided. The clamping instrument includes a pair of handles movably coupled together; a patella support portion operatively connected to the pair of handles via a bottom clamping arm and configured to engage a first side of a patella. The patella support portion included a first pair of flanges each configured to engage a first and second tendon associated with the patella. The clamping instrument also includes a reamer guide configured to engage a second side of the patella. The reamer guide includes a second pair of flanges each configured to engage said first and second tendons associated with the patella. The clamping instrument is configured to operably engage the first and second tendons associated with the patella between the first and second pairs of flanges by application of a squeezing motion to the pair of handles to bring each handle toward the other.

In some embodiments, a system for clamping a patella is provided. The system includes a patellar clamp comprising a pair of handles movably coupled together, a patella support portion operatively connected to the pair of handles via a bottom clamping arm and configured to engage a first side of a patella, the patella support portion including a first pair of flanges each configured to engage a first and second tendon associated with the patella and a plurality of reamer guides, each reamer guide of said plurality having a different diameter than each other reamer guide of said plurality to allow a user to select an appropriately-sized reamer guide, wherein each reamer guide is configured to engage a second side of the patella, each reamer guide including a second pair of flanges configured to engage said first and second tendons associated with the patella.

In some embodiments, a method of clamping a patella is provided. The method includes selecting, from a plurality of reamer guides, a reamer guide configured to enable reaming a predetermined portion of a patellar surface. The selected reamer guide is configured with a first pair of flanges extending from the reamer guide. The method also includes attaching the selected reamer guide to a patellar clamp including a pair of handles and a bottom clamping arm with a patellar support portion and a second pair of flanges. The method includes placing the patellar clamp in an open position, positioning an everted and rotated patella between the selected and attached reamer guide and the patellar support portion of the bottom clamping arm, and squeezing the pair of handles together in a closing motion, causing the selected and attached reamer guide to lower toward the patella and the first pair of flanges and the second pair of flanges to operably engage the quadriceps tendon and patellar tendon.

While the foregoing description and drawings represent illustrative embodiments of the present disclosure, it will be understood that various additions, modifications and substitutions can be made therein without departing from the spirit and scope and range of equivalents of the accompanying claims. In particular, it will be clear to those skilled in the art that the present invention can be embodied in other forms, structures, arrangements, proportions, sizes, and with other elements, materials, and components, without departing from the spirit or essential characteristics thereof. In addition, numerous variations in the methods/processes. One skilled in the art will further appreciate that the embodiments can be used with many modifications of structure, arrangement, proportions, sizes, materials, and components and otherwise, used in the practice of the disclosure, which are particularly adapted to specific environments and operative requirements without departing from the principles described herein. The presently disclosed embodiments are therefore to be considered in all respects as illustrative and not restrictive. The appended claims should be construed broadly, to include other variants and embodiments of the disclosure, which can be made by those skilled in the art without departing from the scope and range of equivalents.

What is claimed is:

1. A clamping instrument configured to engage a first and a second tendon associated with a patella of a patient comprising:
    a pair of handles movably coupled together;
    a patella support portion operatively connected to the pair of handles via a bottom clamping arm and configured to engage said patella, the patella support portion including a first pair of flanges each configured to engage said first and said second tendon associated with said patella; and
    a reamer guide configured to engage a side of said patella, the reamer guide including a second pair of flanges each configured to engage said first and second tendons associated with said patella;
    wherein the clamping instrument is configured to operably engage said first and second tendons associated with said patella between the first and second pairs of flanges by application of a squeezing motion to the pair of handles to bring each handle toward the other.

2. The clamping instrument of claim 1, wherein the patella support portion includes a concave-shaped gripping region configured to engage a convex portion of said patella.

3. The clamping instrument of claim 2, wherein the gripping region includes a textured surface treatment configured to grip said patella.

4. The clamping instrument of claim 1, wherein the tendons are the quadriceps and patellar tendons.

5. The clamping instrument of claim 1, wherein the reamer guide is detachably connected to the clamping instrument.

6. The clamping instrument of claim 1, wherein said pair of handles are biased apart by a compression leaf spring.

7. The clamping instrument of claim 1, further comprising a sliding top clamp arm which is slidable up and down on a reamer support column of said bottom clamping arm.

8. The clamping instrument of claim 7, wherein said sliding top clamp arm is pivotably coupled to a lower handle of said pair of handles.

9. A system for clamping a first and a second tendon associated with a patella of a patient, comprising:
    a patellar clamp, comprising:
    a pair of handles movably coupled together; a patella support portion operatively connected to the pair of handles via a bottom clamping arm and configured to engage of said patella, the patella support portion including a first pair of flanges each configured to engage said first and said second tendon associated with said patella; and
    a plurality of reamer guides, each reamer guide of said plurality having a different diameter than each other reamer guide of said plurality, wherein each reamer guide is configured to engage a second side of said patella, each reamer guide including a second pair of flanges configured to engage said first and second tendons associated with said patella.

10. The system of claim 9, wherein each reamer guide of said plurality of reamer guides is detachably connectable to said patellar clamp via a reamer guide mounting bracket.

11. The system of claim 10 wherein said reamer guide mounting bracket comprises: a frontal opening communicating with an internal cavity configured to receive a portion of a reamer guide mounting stem; and a spring-loaded plunger assembly having an elongated plunger with an operating button and spring.

12. The system of claim 9, said patellar clamp further comprising a sliding top clamp arm which is slidable up and down on a reamer support column of said bottom clamping arm.

13. The system of claim 12 wherein said sliding top clamp arm is pivotably coupled to a lower handle of said pair of handles.

14. The system of claim 13 wherein the patella support portion includes a concave-shaped gripping region configured to engage a convex portion of said patella.

15. The system of claim 14 wherein the gripping region includes a textured surface treatment configured to enhance gripping said patella.

* * * * *